United States Patent [19]
Chu

[11] 4,397,784
[45] Aug. 9, 1983

[54] INHIBITORS OF TRANSPEPTIDASE
[75] Inventor: Daniel T. Chu, Vernon Hills, Ill.
[73] Assignee: Abbott Laboratories, North Chicago, Ill.
[21] Appl. No.: 336,808
[22] Filed: Jan. 4, 1982

Related U.S. Application Data

[63] Continuation-in-part of Ser. No. 205,035, Nov. 7, 1980, abandoned.
[51] Int. Cl.$^3$ ............................................. C07D 487/04
[52] U.S. Cl. .............................. 260/245.2 T; 544/359; 546/123; 546/272; 424/250; 424/263; 424/274; 424/256; 260/239 A
[58] Field of Search ................. 260/245.2 T; 546/272, 546/123; 544/359

[56] References Cited
U.S. PATENT DOCUMENTS

| | | | |
|---|---|---|---|
| 3,875,154 | 4/1975 | Rapoport | 260/245.2 T |
| 3,923,796 | 12/1975 | Rapoport | 260/245.2 T |
| 4,210,661 | 7/1980 | Ponsford et al. | 260/245.2 T |
| 4,262,011 | 4/1981 | Christensen et al. | 260/245.2 T |
| 4,281,002 | 7/1981 | Christensen et al. | 260/245.2 T |
| 4,298,741 | 11/1981 | Christensen et al. | 260/245.2 T |

OTHER PUBLICATIONS

Bose et al.; J. Org. Chem., vol. 39, No. 1, pp. 115–116 (1974).

Primary Examiner—Mary C. Lee
Attorney, Agent, or Firm—Dennis K. Shelton

[57] ABSTRACT

New β-lactams of the general structure:

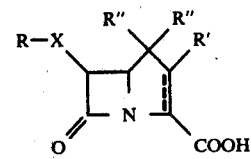

wherein X=O or S; R represents H, loweralkyl, acyl, aryl, or arylloweralkyl; R' is hydrogen, loweralkoxy, loweralkoxyalkyl, loweralkyl, phenylthio or loweralkylmercapto; R" is hydrogen or loweralkyl; and the broken line represents an optional double bond, and certain esters thereof. All compounds are effective antibacterials.

6 Claims, No Drawings

INHIBITORS OF TRANSPEPTIDASE

This application is a continuation-in-part of my prior application Ser. No. 06/205,035 filed Nov. 7, 1980, now abandoned.

DETAILED DESCRIPTION OF THE INVENTION

Many cephalosporin and penicillin derivatives have been synthesized in the past 30 years and many of them have found their way into the arsenal of antibiotic drugs with a broad spectrum of antibacterial activity. However, the bacteria combatted in this fashion have learned to adapt to the attacks by these antibiotics and have formed strains resistant to the antibiotics. It is therefore of great importance to find new antibiotics to which resistance has not yet developed in infectious bacteria. Basic changes in the structure of known antibiotics are particularly well suited to overcome the bacterial resistance to known therapeutics.

The present invention is thus concerned with a new antibacterial, a compound of the formula:

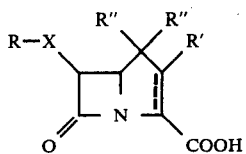   I wherein X is O or S; R represents H, loweralkyl, acyl, aryl, or arylloweralkyl; R' is hydrogen, loweralkoxy, loweralkoxyalkyl, loweralkyl, phenylthio or loweralkylmercapto; R" is hydrogen or loweralkyl; and the broken line represents an optional double bond, and acyloxymethyl esters thereof.

Loweralkyl means 1–4 carbons, linear or branched.

As used herein, the term "acyl" means phenacetyl, phenoxyacetyl, cyanoacetyl, thenylacetyl, p-hydroxyphenylmalonoyl, α-aminophenacetyl, α-sulfophenacetyl, N-benzoylglycylphenylglycyl, a moiety of the formula:

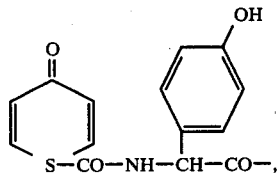

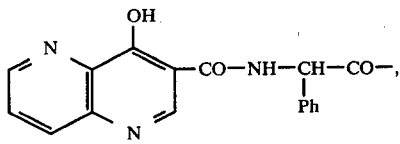

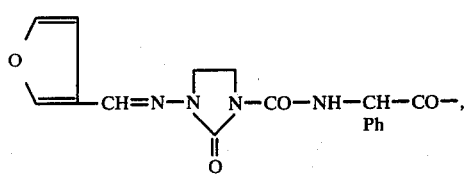

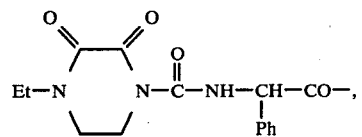

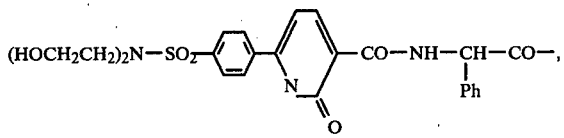

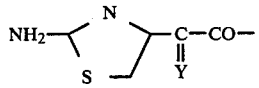

wherein Y is O or NOR", or a mercaptoacetyl of the formula R°SCH₂CO- wherein R° is phenyl, 4-pyridyl, 2-chloro-2-butenyl, allyl or n-butyl.

As used herein, the term "aryl" means phenyl or substituted phenyl.

As used herein, the term "substituted phenyl" means a phenyl moiety substituted with one or more groups independently selected from hydroxy, loweralkyloxy, amino, nitro, halo, loweralkyl, or phenylloweralkyl.

As used herein, the term "arylloweralkyl" means a group having a loweralkyl moiety interposed between X and an aryl moiety.

The compounds wherein R=H and R' is phenylthio or alkoxy and the 2-3 positions are connected by a single bond, are less active than the corresponding unsaturated compounds. All the compounds, however, show activity against numerous infectious and other bacteria, as can easily be demonstrated on cultures of pseudomonas strains at concentrations of 1 to 500 ppm. The new compounds will completely prevent any further growth of *Staph. aureus* and in the higher concentration ranges mentioned will produce a bacteriocidal effect.

The above compounds are prepared by the following scheme, wherein R° is an easily removable group, for instance benzyl, p-nitrobenzyl, 2,2,2-trichloroethyl and other groups well known in the art of temporarily protecting sensitive substituents:

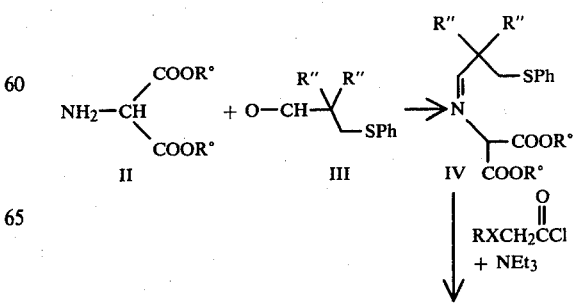

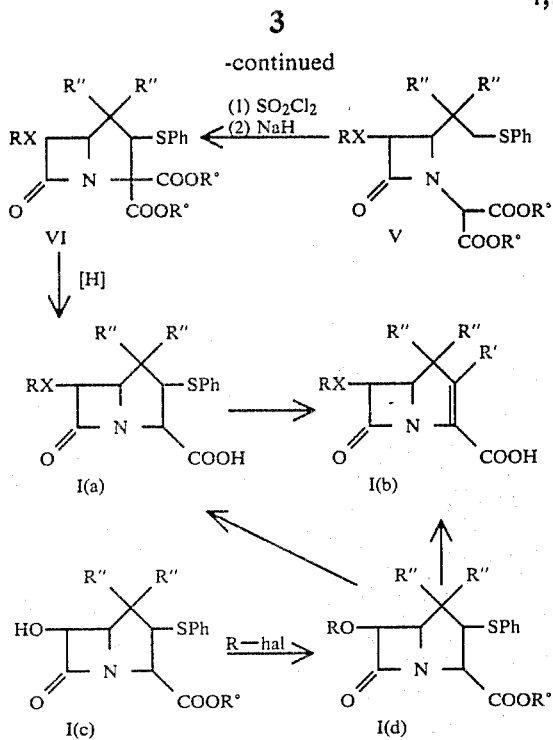

In order to illustrate the manufacture of the compounds of this invention, reference is made to the following examples which, however, are not to be interpreted as limitations of the scope of this invention. In all instances, microanalyses are used to verify the identity of the expected compounds. The designation Ph is used to identify phenyl or phenylene.

EXAMPLE 1

(a) To a solution of 2.00 g. of dibenzylaminomalonate and 1.94 g. of 3-phenylthio-2,2-dimethylpropylaldehyde in 30 ml. methylene chloride is added 10 g. of anhydrous magnesium sulfate. After storing at room temperature for 24 hours, it is filtered and evaporated giving the Schiff base IV (R″=CH₃, R°=benzyl) in high yield.

(b) To a solution of the above Schiff base in 20 ml. of methylene chloride is added 5.6 ml. triethylamine and the reaction mixture is cooled by ice bath. To this, 1.8 ml. methoxyacetyl chloride is added dropwise. One hour after the addition, the ice bath is removed. After two days, it is washed with a saturated sodium chloride solution, dried and evaporated to an oil. It is then chromatographed over silica gel to produce V (R″=CH₃; R°=benzyl) in 30% yield.

(c) To an ice cold solution of 1.38 g. β-lactam V is added 0.183 ml. sulfuryl chloride. After 15 minutes, it is evaporated and redissolved in 20 ml. dimethoxyethane, and 115 mg. of sodium hydride (50% in oil dispersion) is added. The solution is heated at 50° C. for 15 hours. It is then concentrated to nearly dryness, dissolved in methylene chloride and washed with a saturated sodium chloride solution. The organic base is dried over MgSO₄, evaporated and the obtained oil is chromatographed over silica gel to produce VI (R″=CH₃; RX=CH₃O, R°=benzyl).

(d) One gram of the bicyclic β-lactam VI is hydrogenated under hydrogen atmosphere using 10% palladium on charcoal in methanol to give a crude product which is then heated in toluene to give the 6-methoxy-4,4-dimethyl-3-phenylthio-1-azabicyclo[2,0,3]-heptan-7-one-2-carboxylic acid I(a) (RX=CH₃O; R′=PhS; R″=CH₃) in fairly good yield.

(e) To a solution of 3.2 g. the above I(a) in 30 ml. ether is added 1.08 g. of trimethylchlorosilane and 1 g. of triethylamine. After 1 hour it is filtered. The filtrate is concentrated to dryness and redissolved in 20 ml. methylene chloride. To the above solution, 1.72 g. of m-chloroperoxybenzoic is added and refluxed for 10 hours. The reaction product is concentrated to a small volume and then diluted with water and extracted with ether. The organic phase is dried over MgSO₄ and evaporated to produce a solid residue. Repeated precipitation of this material from ether/pentane produces pure 6-methoxy-4,4-dimethyl-1-azabicyclo-[2,0,3]2-hepten-7-one-2-carboxylic acid I(b) (RX=CH₃O; R′=H; R″=CH₃) in a moderate yield.

EXAMPLE 2

By following the preceding Example but substituting the methoxyacetyl chloride with phenoxyacetyl chloride, compounds I (RX=PhO; R″=CH₃) and I(b) (RX=PhO; R′=H; R″=CH₃) are produced.

EXAMPLE 3

By following Example 1 but substituting the methoxyacetyl chloride used there with p-chlorophenoxyacetyl chloride, compounds I(a) and I(b) are made (RX=p-ClPhO; R′=H; R″=CH₃).

EXAMPLE 4

In the described procedure for Example 1, using p-nitrophenoxyacetyl chloride in place of methoxyacetal chloride, compounds I(a) and I(b) are produced (RX=p-NO₂-PhO; R′=H; R″=CH₃).

EXAMPLE 5

By following Example 1, but substituting the methoxyacetal chloride used there with p-methoxyphenoxyacetyl chloride, compounds I(a) and I(b) are obtained (RX=pMeOPhO; R′=H; R″=Me).

EXAMPLE 6

In the described procedure for Example 1, using 2,4-dimethylphenoxyacetyl chloride in place of methoxyacetyl chloride, I(a) and I(b) are produced (RX=2,4-Me₂PhO; R′=H; R″=Me).

EXAMPLE 7

By following Example 1 but substituting the methoxyacetyl chloride with 2-phenylethoxyacetyl chloride, compounds I(a) and I(b) are obtained (RX=PhCH₂CH₂O; R′=H; R″=Me).

EXAMPLE 8

In the described procedure for Example 1, using a compound of formula PhS-CH₂-COCl in place of methoxyacetyl chloride, compounds I(a) and I(b) are made wherein RX=PhS-; R″=CH₃; R′=H.

EXAMPLE 9

In the described procedure for Example 1 (a-d), using a compound of formula PhCH₂-O-CH₂-COCl in place of methoxyacetyl chloride, compound I(a) (RX=HO; R″=CH₃) is prepared in moderate yield.

EXAMPLE 10

(a) To a solution of 2.99 g. of dibenzylaminomalonate and 1.66 g. of 3-phenylthiopropylaldehyde in 30 ml.

methylene chloride is added 10 g. of anhydrous magnesium sulfate. After storing at room temperature for 24 hours, it is filtered and the filtrate is evaporated giving the Schiff base IV (R″=H; R°=benzyl) in good yield.

(b) To a solution of the above Schiff base in 20 ml. of methylene chloride at ice bath temperature is added 5.6 ml. triethylamine followed by 2.44 g. of ethoxyacetyl chloride which is added dropwise. The ice bath is removed after 1 hour. After storing at room temperature for 2 days, it is washed with a saturated sodium chloride solution, dried and concentrated to an oil which is purified by chromatography on silica gel to produce compound V (R°=benzyl; RX=$C_2H_5O$; R″=H) in moderate yield.

(c) By proceeding in accordance with the method shown in Example 1(c), compound VI (R″H; RX=$C_2H_5O$; R°=benzyl) is obtained in moderate yield. In turn, using the procedure of Example 1(d) and 1(e), compounds I(a) and I(b) are produced where RX=$C_2H_5O$; R′=H; R″=H.

EXAMPLE 11

(a) To 3.2 g. of the product of Example 1(d) in 40 ml. of DMF is added 480 mg. sodium hydride as a 50% oil suspension and, after 15 minutes of stirring, 1.7 g. benzylbromide together with a catalytic amount of tetrabutylammonium iodide are added. The mixture is stirred for 4 hours and poured into water. Extraction of the aqueous mixture with $CH_2Cl_2$, drying the extract with $MgSO_4$ and evaporation produces an oil which is purified on neutral alumina; it is identified as the benzyl ester of the compound of Example 1(d).

(b) Treating 4.1 g. of this compound in 20 ml. carbon tetrachloride with 1.33 g. of N-chlorosuccinimide under a sun lamp and with stirring for 5 hours, filtering the mixture and evaporating the filtrate produces the 3-chloro-3-phenylthio analog of the described benzyl ester in excellent yield calculated from the compound of Example 1(d).

(c) A solution of 4.4 g. of this compound in 50 ml. $CH_2Cl_2$ is heated for 3 hours with 1.1 g. of triethylamine. The mixture is then washed with cold water. The organic layer is dried and evaporated to produce a nearly theoretical amount of the analog of the compound of (a) above but containing a double bond between the 2-3 positions.

(d) A solution of 1.33 g. anhydrous $AlCl_3$ in nitromethane is added to a solution of 4.1 g. of the compound of (c) above in 2 g. anisole and 20 ml. $CH_2Cl_2$ under ice cooling. After stirring at room temperature for 5 hours, the mixture is diluted with ethyl acetate, washed with dilute HCl and extracted with 5% aqueous $NaHCO_3$. The aqueous extract is acidified with HCl and then extracted with ethyl acetate. The original layer is washed with water, dried over $MgSO_4$ and evaporated to give a solid residue. After recrystallization from acetone/pentane, the pure unsaturated compound I (RX=Meo, R′=PhS; R″=Me) is obtained in good yield.

EXAMPLE 12

(a) When 5.3 g. of the compound of Example 11(c) in 50 ml. of methanol is stirred with 2.1 g. sodium metaperiodate at 0° C. for 5 hours, followed by refluxing for 15 hours, evaporation and the $CH_2Cl_2$ extraction procedure of Example 1(b), the analog of Example 11(c) is obtained in good yield, carrying a methoxy group in the 3-position in place of the phenylthio group.

(b) Removal of the ester group is carried out as in Example 11(d) to produce a good yield of the unsaturated I (RX=MeO; R′=MeO; R″=Me).

(c) By using butylperiodate in (a) above, the analogous I is obtained with R′ being BuO.

EXAMPLE 13

(a) To a solution of 4.5 g. of the compound of Example 12(a) in 30 ml. $CH_2Cl_2$ is added a mixture of 0.75 ml. ethanethiol and 1 ml. triethylamine. Refluxing for 15 hours and evaporation under reduced pressure produces the ethylmercapto-analog of the compound of Example 11(c) in almost quantitative yield.

(b) Upon ester group removal as in Example 11(d), unsaturated compound I (RX=MeO; R′=EtS; R″=Me) is obtained in very good yield.

(c) By replacing ethanethiol with t-butylthiol, the above process produces the analogous I(b) with R′=t-BuS.

EXAMPLE 14

By following the procedure of Example 12(a) and 12(b) with 4.1 g. of the compound of Example 11(c) but using 20 ml. of methoxyethanol in place of methanol, unsaturated compound I (RX=MeO; R′=MeO$CH_2$C-$H_2O$; R″=Me) is obtained in good yield.

EXAMPLE 15

To a solution of 4.1 g. of the compound of Example 11(b) in 100 ml. dry THF at 0° is added 3.33 ml. of a 3 molar solution of methylmagnesium chloride. After stirring for 1 hour, 2.1 g. sodium periodate is added and the mixture is refluxed for 15 hours. This is followed by the usual work-up using $CH_2Cl_2$ and a carbon column to produce an oil identified as I(b) wherein RX is methoxy, R′ and R″ are methyl and the carboxy group is esterified with benzyl.

Removal of the benzyl ester group in the fashion of Example 11(d) produces the unsaturated compound I (RX=methoxy; R′=Me; R″=Me).

Upon hydrogenating a solution of the latter in THF in the presence of palladium-on-carbon at 40 psig H pressure and room temperature, the analogous, saturated compound is obtained in quantitative yield.

EXAMPLE 16

By the described procedure for Example 15 using 2-methoxyethyl magnesium chloride instead of methylmagnesium chloride, the unsaturated compound I (RX=methoxy; R′=$CH_2CH_2OCH_3$; R″=Me) is prepared.

EXAMPLE 17

(a) To 3.1 g. of the product of Example 9 in 40 ml. of DMF is added 480 mg. sodium hydride as a 50% oil suspension and after 15 minutes of stirring, 1.7 g. benzylbromide together with a catalytic amount of tetrabutylammonium iodide are added. The mixture is stirred for 4 hours and poured into water. Extraction of the aqueous mixture with $CH_2Cl_2$, drying the extract with $MgSO_4$ and evaporation produces an oil which is purified over neutral alumina; it is identified as the benzyl ester of the compound of Example 9.

(b) To a solution of 4 g. of this compound in 30 ml. methylene chloride is added 1 ml. of pyridine followed by dropwise addition of 1.7 g. of phenoxyacetyl chloride in 10 ml. of methylene chloride. After 15 hours, the mixture is diluted with methylene chloride and washed with a saturated sodium chloride solution, dried and evaporated to an oil. It is then chromatographed over alumina to produce 2(d) (RX=PhOCH$_2$CO$_2$; R''=CH$_3$; R°=PhCH$_2$).

(c) 5.3 g. of this compound is hydrogenated under hydrogen atmosphere using 10% palladium-on-charcoal in methanol to give compound I(a) (RX=PhOCH$_2$COO; R''=CH$_3$).

(d) In the described procedure for Example 1(e), the compound in 17(c) is converted to I(b) (RX=PhOCH$_2$CO$_2$; R'=H; R''=CH$_3$).

EXAMPLE 18

By following Example 17 using cyanoacetyl chloride in place of the phenoxyacetyl chloride, compounds I(a) and I(b) are made (RX=CNCH$_2$CO$_2$; R'=H; R''=CH$_3$).

EXAMPLE 19

In the described process for Example 17, using thenylacetyl chloride instead of phenoxyacetyl chloride, compounds I(a) and I(b) are produced

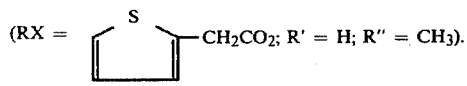

In similar fashion, the use of various other acyl groups frequently used in the cephalosporin or penicillin series leads to the saturated compounds of structure I wherein R' is phenylthio, alkoxy, alkylthio, alkoxyalkyl and R'' is H and ultimately the unsaturated analogs compound I(b) with R' being H or loweralkyl. The following acyl groups are used:

R = phenacetyl
  = p-hydroxyphenylmalonoyl
  = α-sulfophenylacetyl
  = aminothiazylacetyl
  = 5-aminoglutaroyl
  = α-aminophenacetyl

EXAMPLE 20

To 2.1 g. of the product in Example 1(e) in 25 ml. DME is added 480 mg. sodium hydride as a 50% oil suspension and after 5 minutes of stirring, 1.5 g. of chloromethyl pivalate is added. After 2 hours, the mixture is evaporated and redissolved in methylene chloride and washed with water, dried and evaporated. It is then purified through alumina yielding the 2-pivaloxylmethyl ester of the 2-carboxy β-lactam of Example 1(e).

EXAMPLE 21

In the described procedure of Example 20, using -pivaloyloxy ethyl chloride instead of chloromethyl pivalate, the -pivaloyloxy ethyl ester analog of the ester of Example 20 is made.

EXAMPLE 22

By following Example 20, but substituting the product of Example 1(e) by the product of 1(d), the pivaloyloxylmethyl ester of the 2-carboxy β-lactam of Example 1(d) is made in good yield.

In all cases, the saturated and unsaturated 3-substituted derivatives and the unsaturated 3-unsubstituted compounds, with or without R''-alkyl substitutions are active against pseudomonas. The latter compounds are best obtained from the unsaturated 3-phenylthio- compounds in yields of 65–80% and are ordinarily more active, i.e., they require a lower dosage than the 3-phenylthio compounds. In vitro activity of the latter compounds are generally found at 100–500 ppm; the unsaturated analogs are active at 1–250 ppm against numerous infections, gram-positive bacteria.

One of the most important steps of the reaction sequence leading to the new compounds of this invention is the ring closure step for the azetidine ring. The preferred method for this reaction consists of treating compound IV in an inert organic solvent, for instance methylene chloride or DME, with an appropriate acetyl halide in the presence of an acid acceptor at a temperature below room temperature, preferably between −25° C. and +10° C. Acid acceptors include trialkylamines, such as trimethylamine or triethylamine. The obtained β-lactam V is then easily converted to the desired bicyclic β-lactam VI by chlorination and a basic cyclization reaction. The free acid (I) is prepared by hydrogenating VI. A preferred method for this step is catalytic hydrogenation, using a noble metal catalyst, although Raney nickel can also be used. Among noble metals, palladium is preferred, although platinum or ruthenium can be used as well.

We claim:

1. A compound of the formula

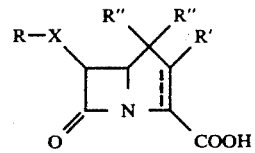

wherein X=O or S; R represents H, loweralkyl, phenacetyl, phenoxyacetyl, cyanoacetyl, thenylacetyl, p-sulfophenacetyl, N-benzoylglycylphenylglycyl, a moiety of the formula

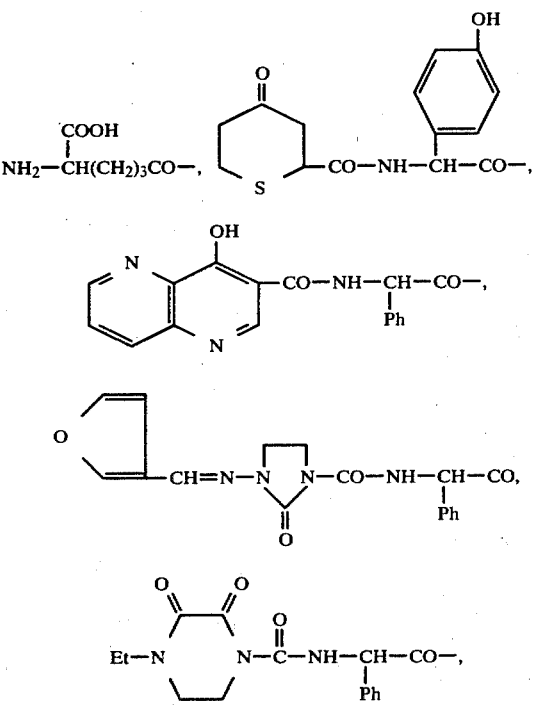

-continued

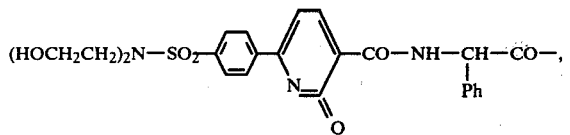

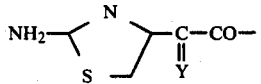

wherein Y is O or NOR", a mercaptoacetyl of the formula R°SCH₂CO- wherein R° is phenyl, 4-pyridyl, 2-chloro-2-butenyl, allyl or n-butyl, phenyl, phenylloweralkyl, substituted phenyl or substituted phenyllower- alkyl, wherein substituted phenyl is a phenyl moiety substituted with one or more groups independently selected from hydroxy, loweralkoxy, amino, nitro, halo, loweralkyl or phenylloweralkyl; R' is hydrogen, loweralkoxy, loweralkoxyalkyl, loweralkyl, phenylthio or loweralkylmercapto; R" is hydrogen or loweralkyl; and the broken line represents an optional double bond, and acyloxymethyl esters thereof.

2. An unsaturated compound of claim 1 wherein R is H.

3. A compound of claim 2 wherein each R" is methyl.

4. A compound of claim 3 wherein R' is PhS.

5. The compound of claim 4 wherein X is O.

6. The 2-pivaloxymethyl ester of the compound of claim 5.

* * * * *